(12) United States Patent
Sakaguchi

(10) Patent No.: US 7,800,748 B2
(45) Date of Patent: Sep. 21, 2010

(54) EDGE INSPECTION APPARATUS

(75) Inventor: Naoshi Sakaguchi, Kawasaki (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 12/292,010

(22) Filed: Nov. 10, 2008

(65) Prior Publication Data
US 2009/0086196 A1  Apr. 2, 2009

Related U.S. Application Data

(63) Continuation of application No. PCT/JP2007/059471, filed on May 7, 2007.

(30) Foreign Application Priority Data

May 9, 2006 (JP) ............................. 2006-129894
May 9, 2006 (JP) ............................. 2006-129895

(51) Int. Cl.
*G01N 21/00* (2006.01)
(52) U.S. Cl. ................... 356/237.2; 356/237.1
(58) Field of Classification Search .... 356/237.1–237.5
See application file for complete search history.

(56) References Cited

U.S. PATENT DOCUMENTS

| 6,545,752 B1 | 4/2003 | Swan et al. |
| 6,906,794 B2 | 6/2005 | Tsuji |
| 6,947,588 B2 * | 9/2005 | Sim ........................... 382/149 |
| 7,340,087 B2 * | 3/2008 | Watkins et al. .............. 382/145 |
| 2003/0030050 A1 | 2/2003 | Choi |
| 2003/0030795 A1 | 2/2003 | Swan et al. |
| 2005/0036671 A1 | 2/2005 | Watkins et al. |
| 2005/0280807 A1 | 12/2005 | Backhauss et al. |
| 2007/0258085 A1 * | 11/2007 | Robbins et al. .......... 356/237.4 |

FOREIGN PATENT DOCUMENTS

| JP | A-11-351850 | 12/1999 |
| JP | A-2004-518293 | 6/2004 |
| JP | A-2006-5360 | 1/2006 |
| JP | A-2006-17685 | 1/2006 |
| JP | A-2006-64975 | 3/2006 |
| JP | A-2007-59640 | 3/2007 |
| WO | WO 02/059960 A1 | 8/2002 |
| WO | WO 03/028089 A1 | 4/2003 |
| WO | WO 2005/008170 A2 | 1/2005 |
| WO | WO 2005/115689 A1 | 12/2005 |

* cited by examiner

*Primary Examiner*—Michael P Stafira
(74) *Attorney, Agent, or Firm*—Oliff & Berridge, PLC

(57) ABSTRACT

An edge inspection apparatus includes: an illumination means 5 that illuminates an edge of a flat subject with diffused light from a position other than directly above or directly below a surface or a reverse surface of the subject; an imaging means 4 that takes an image of the edge from a position in a direction perpendicular to a plane parallel to the surface or the reverse surface of the subject at the same time; and an inspection means 7 that inspects conditions of a portion of the edge, which is inclined with respect to the surface or the reverse surface using the image obtained by the imaging means.

15 Claims, 6 Drawing Sheets

EDGE INSPECTION APPARATUS

This application is a continuation of International Application No. PCT/JP2007/059471 filed May 7, 2007.

INCORPORATION BY REFERENCE

The disclosures of the following priority application and International application are herein incorporated by reference:
Japanese Patent Application No. 2006-129894 (filed May 9, 2006)
Japanese Patent Application No. 2006-129895 (filed May 9, 2006)
International Application No. PCT/JP2007/059471 filed May 7, 2007

BACKGROUND OF THE INVENTION

1. Field of the Invention

The present invention relates to an edge inspection apparatus for inspecting an edge of a flat substrate such as a semiconductor wafer or a liquid crystal glass substrate.

2. Description of Related Art

The degree of integration of circuit patterns formed on a semiconductor wafer has recently been increasing year by year. The number of types of materials used in surface processing of wafers in production processing is also increasing in accompaniment with this. A boundary of a film created as a result of surface processing exists in the vicinity of an edge of a wafer. Observation of the vicinity of the edge of the wafer is therefore important in production processing. Management of defects in the vicinity of the surface of the edge influences the yield for circuits obtained from the wafer.

Because of this, in the related art, the vicinity of the edge of a flat substrate such as, for example, a semiconductor wafer is observed from a plurality of directions and the presence or absence of foreign matter, peeling of the film, bubbles within the film, wrapping around of the film, and cutting notches is inspected for.

Apparatus that detect foreign matter using light scattered as a result of illumination with laser light etc. exist as inspection apparatus for carrying out this inspection (refer to patent document 1).

(Patent Document 1) Japanese Laid-open Patent Publication No. H11-351850.

For example, when the edge of the semiconductor wafer is inclined with respect to a surface of the semiconductor, it is difficult for inspection apparatus of the related art to inspect conditions of this inclined surface.

It is therefore an object of the present invention to provide edge inspection apparatus capable of accurately inspecting conditions of an edge of a flat subject.

SUMMARY OF THE INVENTION

An edge inspection apparatus according to a first aspect of the present invention includes: a first illumination unit that illuminates an edge of a flat subject with diffused light from a position other than directly above or directly below a surface or a reverse surface of the subject; an imaging unit that takes an image of the edge from a position in a direction perpendicular to a plane parallel to the surface or the reverse surface of the subject at the same time; and an inspection unit that inspects conditions of a portion of the edge, which is inclined with respect to the surface or the reverse surface using the image obtained by the imaging unit.

An edge inspection apparatus according to a second aspect of the present invention includes: a first illumination unit that illuminates an edge of a flat subject with illuminating light of a high directivity from a position other than directly above or directly below a surface or a reverse surface of the subject; an imaging unit that takes an image of the edge from a position in a direction perpendicular to a plane parallel to the surface or the reverse surface of the subject; and an inspection unit that inspects conditions of a portion of the edge, which is inclined with respect to the surface or the reverse surface using the image obtained by the imaging unit.

An edge inspection apparatus according to a third aspect of the present invention includes: a first illumination unit capable of illuminating an edge of a flat subject with diffused light and illuminating light of a high directivity from a position other than directly above or directly below a surface or a reverse surface of the subject; an imaging unit that takes an image of the edge from a position in a direction perpendicular to a plane parallel to the surface or the reverse surface of the subject; an inspection unit that inspects conditions of a portion of the edge, which is inclined with respect to the surface or the reverse surface using the image obtained by the imaging unit; and a control unit that switches illumination light from the first illumination unit between the diffused light and the illuminating light with a high degree of directivity.

An edge inspection apparatus according to a fourth aspect of the present invention includes: an imaging unit that takes an image of an edge of a flat subject from a position in a direction perpendicular to a plane parallel to a surface or reverse surface of the subject; and an inspection unit that inspects conditions of a portion of the edge, which is inclined with respect to the surface or the reverse surface by comparing an image obtained by the imaging unit and a reference image stored in advance.

DESCRIPTION OF PREFERRED EMBODIMENTS

The following is a description of preferred embodiments of the present invention.

First Embodiment

Figure 1:
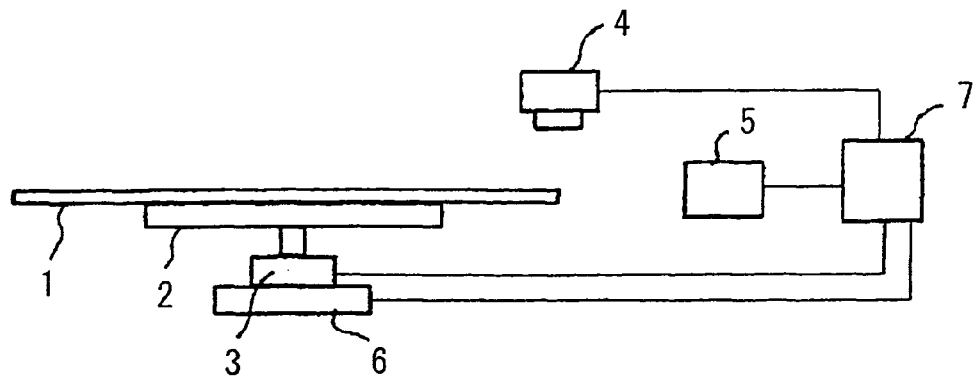
FIG. 1 is a diagram showing a configuration for an edge inspection apparatus according to embodiments of the present invention.

FIG. 1 is a diagram showing a configuration for an edge inspection apparatus according to embodiments of the present invention. A semiconductor wafer 1 is mounted so as to be supported using suction on a support table 2. A rotational drive unit 3 rotates the support table 2. The semiconductor wafer 1 supported on the support table 2 can then be rotated as a result.

A camera 4 is installed above the semiconductor wafer 1 and is capable of taking images of an outer peripheral edge of the semiconductor wafer 1 from above. The camera 4 is preferably arranged at a position facing the edge of the semiconductor wafer 1 so that an imaging optical axis is perpendicular with respect to a surface of the semiconductor wafer 1. However, any position is acceptable providing that it is possible to take images of the edge of the semiconductor wafer 1. It is also possible to arrange the camera 4 below the semiconductor wafer 1 and take images of the edge of the reverse surface of the semiconductor wafer 1.

The camera 4 has an epi-illumination function and is capable of taking an image while epi-illuminating at least part of an imaging range. An optical system for epi-illumination for the camera 4 is a telecentric optical system. It is also possible for the epi-illumination function to be made to go on and off as necessary.

An illumination apparatus 5 is apparatus for illuminating the edge of the semiconductor wafer 1 from a lateral direction and carries out illumination using diffused light or illumination using illuminating light of a high degree of directivity. The illuminating light from the illumination apparatus 5 illuminates the wafer (a) in directions other than above the surface of the wafer, (b) in directions other than below the surface of the wafer, (c) in directions other than above the reverse surface of the wafer, and (d) in directions other than below the reverse surface of the wafer. In this embodiment, the illumination apparatus 5 is installed so that illumination can be carried out in a direction parallel with the front and reverse surfaces of the semiconductor wafer 1, i.e. from an outer peripheral direction of the semiconductor wafer 1.

The illumination apparatus 5 can switch illumination between illumination due to diffused light and illumination due to illuminating light with high directivity under the control of a control unit 7. The illumination apparatus 5 is also capable of switching light sources in the event of carrying out either illumination due to diffused light or illumination due to illuminating light with high directivity. The light sources are, for example, a halogen lamp and an LED and it is possible to switch over light sources so as to change the wavelength of the illuminating light. It is also possible to change the color of the illuminating light and to adjust white balance as a result by changing the wavelength of the illuminating light.

A horizontal drive unit 6 causes the support table 2 and the rotational drive unit 3 to move in a horizontal direction. Here, "horizontal direction" is a direction parallel to the surface the semiconductor wafer 1 of the support table 2 in the drawings is mounted on and is a lateral direction in the drawings. This driving in a horizontal direction is carried out in order to correct so-called eccentricity resulting from the center of the semiconductor wafer 1 and the center of rotation of the support table 2 not coinciding while the semiconductor wafer 1 is mounted on the support table 2.

The control unit 7 controls the operation of the rotational drive unit 3, the camera 4, the illumination apparatus 5, and the horizontal drive unit 6 and detects defects at the edge of the semiconductor wafer 1 based on images from the camera 4.

Figure 2:
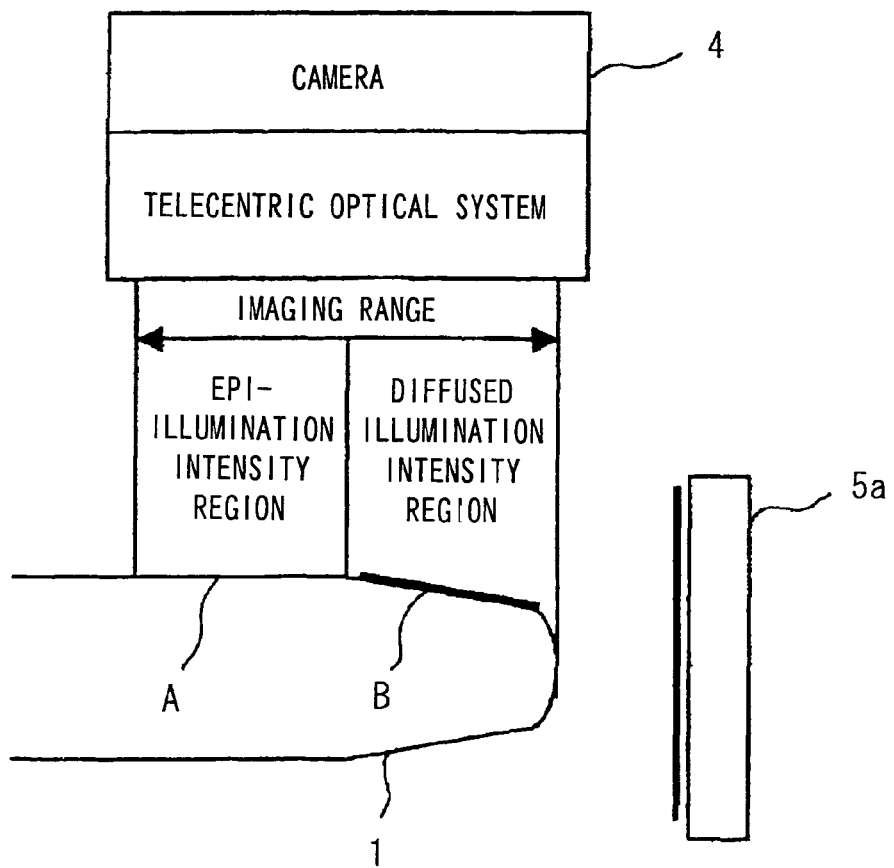
FIG. 2 is a diagram illustrating an image of an edge of a semiconductor wafer 1 taken by a camera 4 of the edge inspection apparatus according to a first embodiment of the present invention.

Next, a description is given of a configuration for acquiring images of the edge of the semiconductor wafer 1 using the camera 4. FIG. 2 is a view illustrating when an image of the edge of the semiconductor wafer 1 is taken using the camera 4 of the edge inspection apparatus according to the first embodiment of the present invention. In FIG. 2, the illumination apparatus 5a illuminates the edge of the semiconductor wafer 1 with diffused light as a result of a diffusing plate being provided to the front of the light source.

A region on the upper surface of the wafer shown by the letter A and an inclined surface region inclined with respect to the upper surface of the wafer at the edge of the semiconductor wafer 1 shown by the letter B in FIG. 2 exist. The region A is then epi-illuminated by the telecentric optical system of the camera 4 and a bright field image is taken for the region A by the camera 4 based on this epi-illumination. Illumination by the illumination apparatus 5 is switched over to illumination using diffused light and a bright field image is taken of the region B by the camera 4 using illumination using diffused light. In the drawing, numeral 5a is assigned to the illumination apparatus 5 when diffused light illumination is being used and numeral 5b is assigned to the illumination apparatus 5 when illumination using illuminating light of high directivity is being used. It is therefore possible to take images of bright field images for both region A and region B at the same time using the camera 4.

Before taking images using the camera 4, the control unit 7 adjusts the intensity of the epi-illumination by the camera 4 and the intensity of the illuminating light of the illumination apparatus 5 so that the intensity of the region A and the intensity of the region B are within an intensity range photographable by the camera 4 using the image taken by the camera 4. The control unit 7 adjusts the white balance of the image being inputted to the camera 4 by switching over the light sources of the illumination apparatus 5.

Figure 3A:
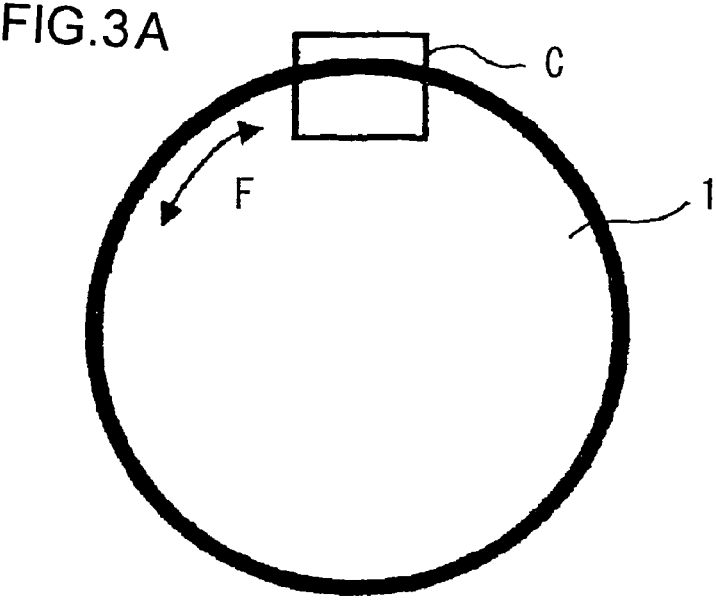
FIGS. 3A to 3D are diagrams illustrating a procedure for detecting defects using photographed images.
Figure 3B:
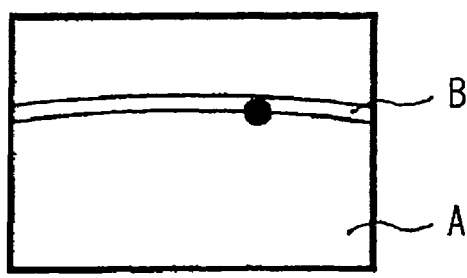
Figure 3C:
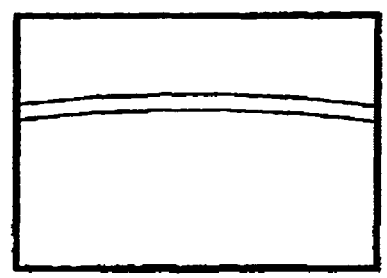

FIGS. 3A to 3D is a view illustrating a procedure for detecting defects using a photographed image. A region shown by C of the upper surface of the semiconductor wafer 1 of FIG. 3A is the imaging range of the camera 4. FIG. 3C is an image taken in advance for a non-defective wafer that is an image of the region C. FIG. 3B is an image of the region C of the semiconductor wafer 1 that is a target of inspection.

Figure 3D:
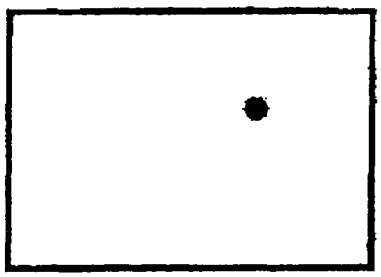

The image of the non-defective wafer of FIG. 3C is stored in the control unit 7 in advance. The control unit 7 then makes a comparison with the image of FIG. 3B that is an image of the semiconductor wafer 1 that is the target of inspection taken by the camera 4. This comparison is carried out by acquiring an image of FIG. 3D by subtracting each pixel value corresponding to the image of FIG. 3C from each pixel value of the image of FIG. 3B. The image of FIG. 3D is a defect image indicating defects. If there is no defect, the image of FIG. 3D should be an image that is white overall but where black portions are defects, as shown in FIG. 3D.

Figure 4:
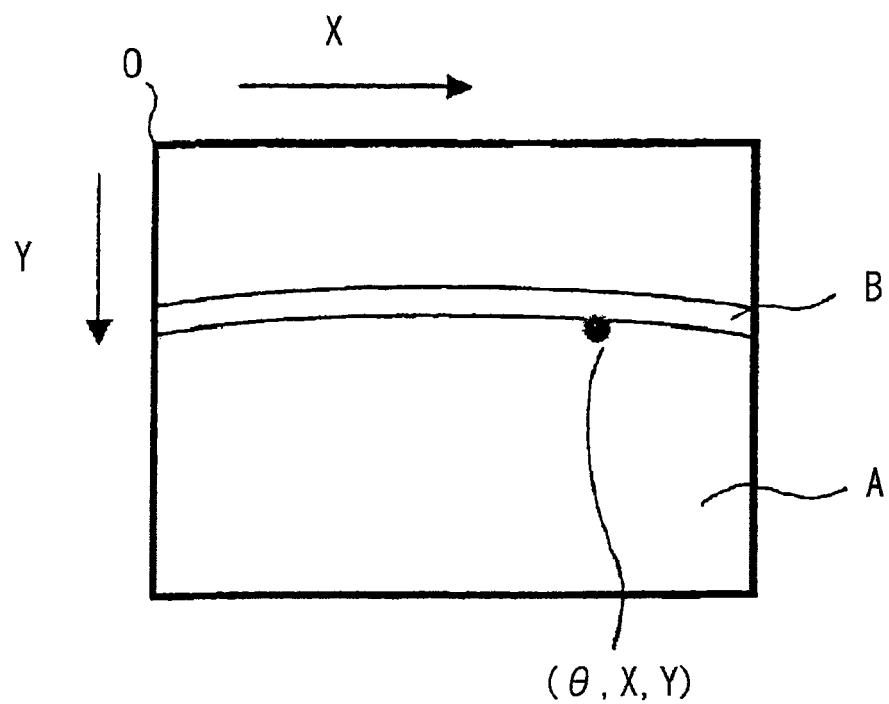
FIG. 4 is a diagram illustrating a coordinate system for specifying a position of a detected defect.

FIG. 4 is a view illustrating a coordinate system for specifying a position of a detected defect. FIG. 4 shows an image taken by the camera 4 where a coordinate system taking a predetermined point within the image as an origin is defined. In FIG. 4, a point at the upper left of the image is defined as an origin O, the horizontal direction is defined as the X-axis, and the downward direction is defined as the Y-axis. It is then possible to obtain X and Y and to specify a position within the image using a number of pixels from the origin to a given position.

A value θ is used to specify a position within the semiconductor wafer 1. The value θ is now explained. It is possible to rotate the semiconductor wafer 1 as shown by an arrow F in FIG. 3A. The control unit 7 can obtain an image of the edge for the entire periphery of the semiconductor wafer 1 by controlling rotation of the semiconductor wafer 1 and controlling the taking of images by the camera 4 at each rotation angle position. The rotation angle position can be specified using a rotation angle from a certain reference angle position. The reference angle position can be decided by detecting notches or orientation flats provided at the edge of the semiconductor wafer 1 using well-known technology. The position of the edge of the semiconductor wafer can be specified using the rotation angle θ from the reference position and a coordinate value (θ, X, Y) due to the positions X and Y within the photographed image occurring at the position of this rotation angle θ. In FIG. 4, the position of a black spot that is a defect is shown by the coordinates (θ, X, Y).

Figure 5:
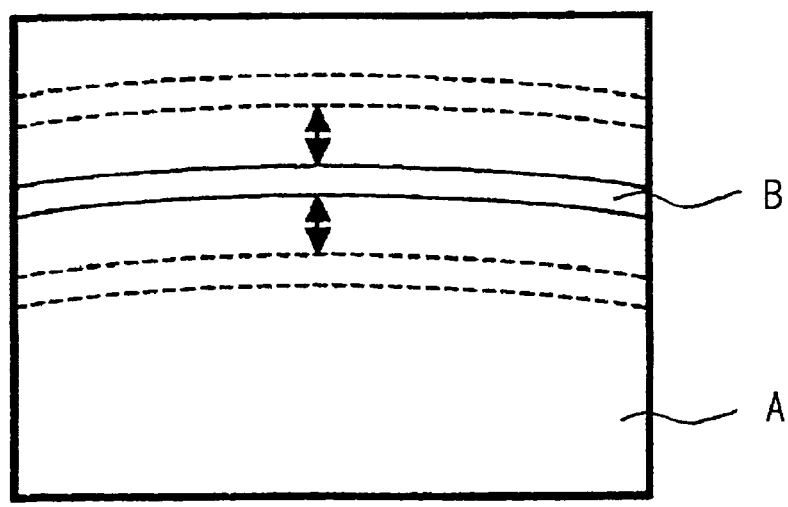
FIG. 5 is a diagram illustrating correction of eccentricity resulting from a center of the semiconductor wafer 1 and a center of rotation of a support table 2 not coinciding while the semiconductor wafer 1 is mounted on the support table 2.

FIG. 5 is a diagram illustrating correction of eccentricity due to the center of the semiconductor wafer 1 and the center of rotation of the support table 2 not coinciding while the semiconductor wafer 1 is mounted on the support table 2. It is difficult to make the center of the semiconductor wafer 1 and the center of rotation of the support table 2 coincide while mounting the semiconductor wafer 1 on the support table. When the support table 2 is then rotated so that images of the edge of the semiconductor wafer 1 are taken consecutively by the camera 4 at a plurality of rotation positions, each edge position for the plurality of photographed images shifts depending on the rotation position.

As shown in FIG. 5, respective positions of the region B of the outer peripheral edge of the semiconductor wafer 1 within the plurality of images taken by the camera 4 depend on the rotation position and change from the position shown by the broken line at the upper part within the image to the position shown by the broken line at the lower part. The eccentricity can be obtained by detecting the position of the outer edge using well-known technology while rotating the semiconductor wafer 1 for 360 degrees.

In this embodiment, the eccentricity at each rotation angle position is obtained in advance and is stored in a manner corresponding to each rotation angle position. With each taking of an image at each rotation angle position, the support table 2 is caused to move in a horizontal direction by each extent of eccentricity obtained in advance so that the position of the region B within the image becomes the position shown by the solid line in FIG. 5. Driving of the support table 2 is controlled as a result of the horizontal drive unit 6 being controlled by the control unit 7.

As shown in FIG. 5, part of a circular arc of an outer periphery of the wafer in an image of the edge of the semiconductor wafer 1 can be approximated as a straight line. The support table 2 is therefore moved in a horizontal direction, the semiconductor wafer 1 moves in the Y-direction shown in FIG. 4, and the coordinates of the outer periphery edge of the edge image for the semiconductor wafer 1 are corrected. An image of the edge of the semiconductor wafer 1 is then taken by the camera 4. An image where the influence of center shift (eccentricity) of the support table 2 and the semiconductor wafer 1 can be eliminated can be obtained by correcting the position of the outer periphery image for the wafer by moving the semiconductor wafer 1 in the Y-direction every rotation angle position.

Detection of defects at the edge of the semiconductor wafer 1 is carried out as explained above using a plurality of images taken at each rotation angle position. Defect detection is explained using FIGS. 3A to 3D and is now explained in more detail. As explained above, detection of defects is carried out by comparing an image taken as shown in FIG. 3A with an image of a non-defective wafer taken in advance as shown in FIG. 3C.

The rotation angle position to be taken during inspection can be set in advance. It is possible to set the number of rotation angle positions at which images are taken so as to make it possible to take images of the edge for the entire outer periphery of the semiconductor wafer 1 and it is possible to set prescribed inspection angle positions. The non-defective wafer images are images acquired by taking images at the same positions as for the rotation angle positions for taking pictures during inspection, are taken in advance and stored in advance in the control unit 7. Defect detection is then carried out by comparing images taken at each rotation angle position (FIG. 3B) and corresponding non-defective wafer images (non-defective wafer images for the same rotation angle positions as for the taken images). This operation is carried out for each image taken at each rotation angle position.

Non-defective wafer images do not have to be images stored in advance that correspond to all of the rotation angle positions. It is also possible to detect defects by storing an image for a rotation angle position for a certain part of a non-defective wafer and comparing this image and images taken at each rotation angle position, providing that there is no substantial change in the edge image for the non-defective wafer due to the rotation angle position.

It is also possible to carry out defect detection in the following manner even when there is no image for a non-defective wafer. In this embodiment, each image of the edge at a plurality of rotation angle positions is obtained by rotating the semiconductor wafer 1. Defect detection can then be carried out by comparing an image at a certain rotation angle position and an image at another rotation angle position. This is because an image including a defect will differ substantially from the other image. For example, in the case of detecting a defect for an image at a certain rotation angle position, it is possible to make a comparison with an image acquired for a neighboring rotation angle position. If the neighboring portions are normal, there will not be a substantial difference. It can then be determined that a defect exists when there is a difference of a certain magnitude between the images. Naturally, defect detection by comparing with an image at a position that is not a neighboring rotation angle position is also possible.

In this way, even if there is no image of a non-defective wafer, it is possible to carry out defect detection by making a comparison with an image of an edge for another position of the semiconductor wafer that is the target of inspection.

Second Embodiment

Figure 6:
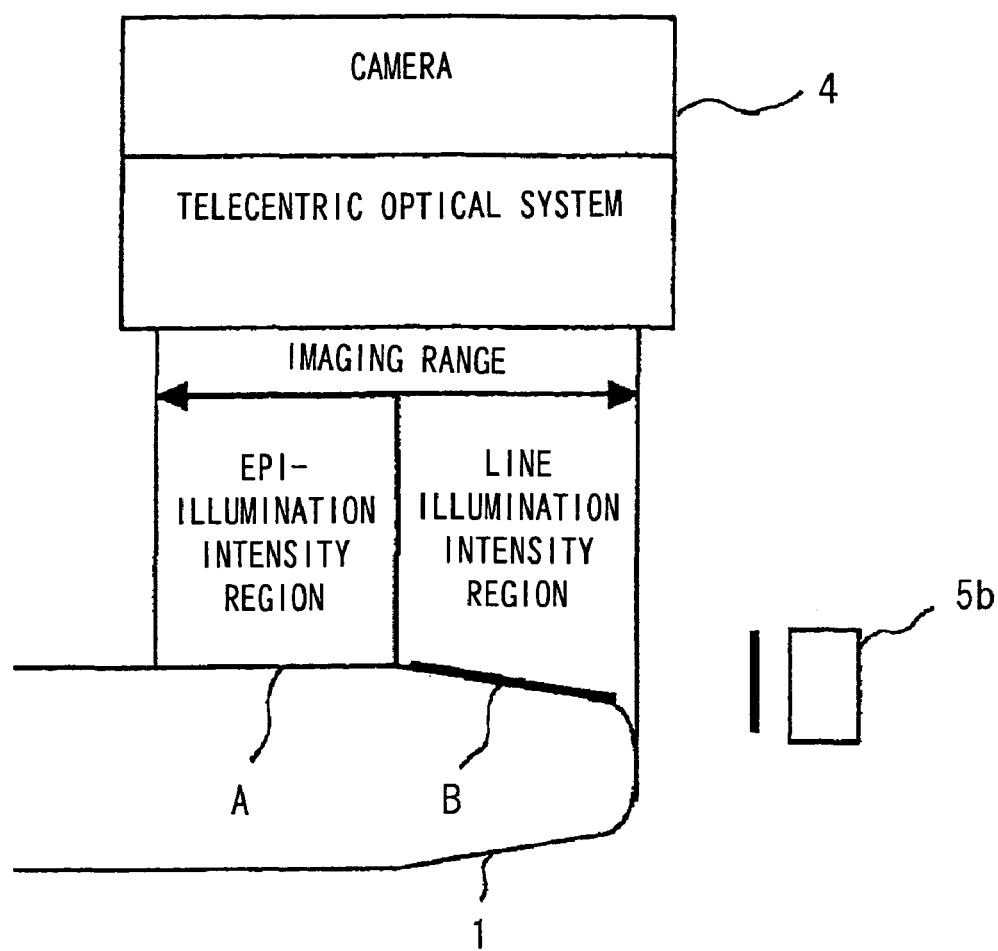
FIG. 6 is a diagram illustrating an image taken of an edge of the semiconductor wafer 1 by the camera 4 of the edge inspection apparatus according to a second embodiment of the present invention.

FIG. 6 is a diagram of a case where an image of an edge of the semiconductor wafer 1 is taken by a camera 4 of an edge inspection apparatus according to a second embodiment of the present invention. In FIG. 6, illumination by the illumination apparatus 5 is switched over to line illumination by an optical fiber by the control unit 7 and illumination of high directivity is carried out. In the drawings, the illumination apparatus is assigned numeral 5b when illumination of a high degree of directivity is carried out. In this embodiment also, as in the case in FIG. 2, epi-illumination is carried out by the telecentric optical system of the camera 4 on a portion of the region A of the semiconductor wafer 1 and a bright field image is taken for the region A based on this epi-illumination by the camera 4. A dark field image is then taken by the camera 4 of the region B using line illumination from the illumination apparatus 5b. It is therefore possible to take a bright field image of the region A and a dark field image of the region B at the same time using the camera 4.

The edge inspection apparatus according to the second embodiment differs to the edge inspection apparatus of the first embodiment shown in FIG. 2 in that a dark field image is taken of the region B. With the inspection for the presence or absence of flaws at the edge of the semiconductor wafer 1 or inspection of the presence or absence of foreign matter such as contaminants that have become affixed, it is possible to easily detect foreign matter by using a dark field image.

Third Embodiment

Figure 7:
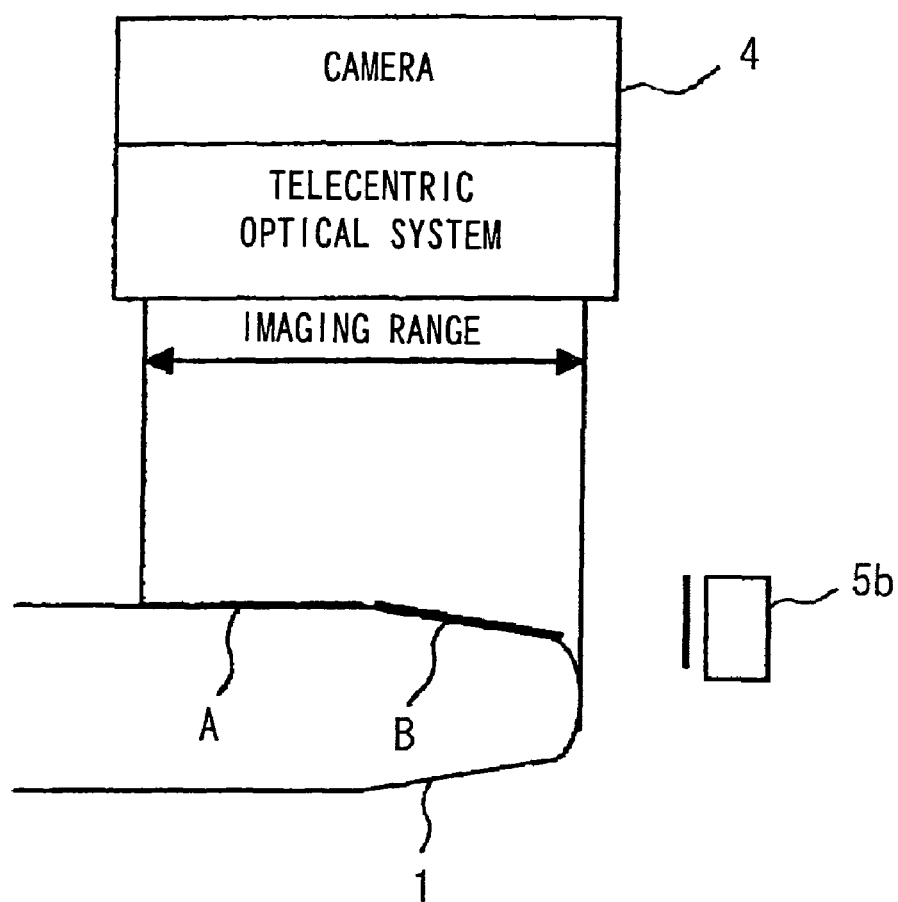
FIG. 7 is a diagram illustrating an image taken of an edge of the semiconductor wafer 1 taken by the camera 4 of the edge inspection apparatus according to a third embodiment of the present invention.

FIG. 7 is a diagram of a case where an image of the edge of the semiconductor wafer 1 is taken by the camera 4 of the edge inspection apparatus according to a third embodiment of the present invention. In this embodiment, line illumination light is irradiated from the illumination apparatus 5b as in the second embodiment of FIG. 6. However, epi-illumination from the camera 4 is not carried out. Namely, in this embodiment, as a result of control by the control unit 7, epi-illumination is not carried out by the camera 4, illumination by the illumination apparatus 5 is switched over to line illumination, and dark field images are taken for the region A and the region B using the camera 4.

As described above, it is straightforward to detect foreign matter using dark field images in inspection of the presence or absence of flaws in the edge of the semiconductor wafer 1 and inspection of the presence or absence of foreign matter such as contaminants affixed to the edge. In this embodiment, detection of foreign matter is straightforward for both region A and region B.

Fourth Embodiment

Figure 8:
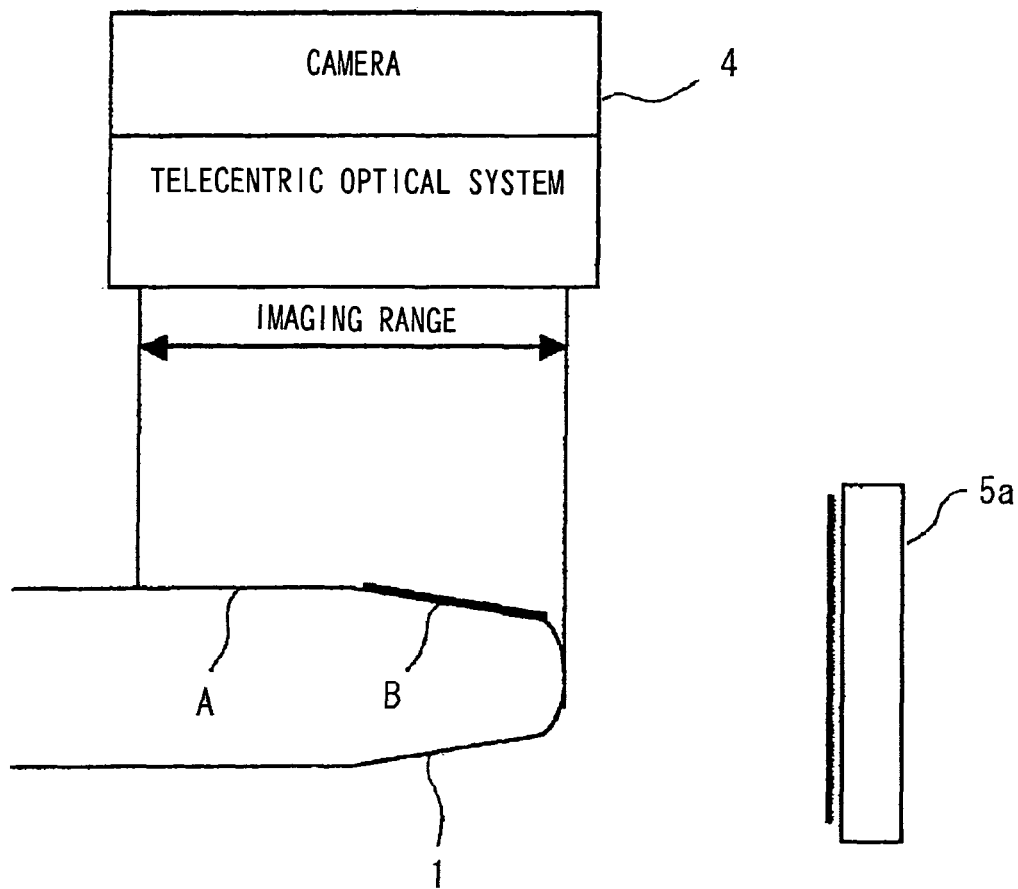
FIG. 8 is a diagram illustrating an image of an edge of the semiconductor wafer 1 taken by the camera 4 of the edge inspection apparatus according to a fourth embodiment of the present invention.

FIG. 8 is a diagram of a case where an image of the edge of the semiconductor wafer 1 is taken by the camera 4 of the edge inspection apparatus according to a fourth embodiment of the present invention. In this embodiment, illumination is carried out using diffused light from the illumination apparatus 5a as in the first embodiment of FIG. 2. However, epi-illumination from the camera 4 is not carried out in the same way as for the third embodiment. Namely, in this embodiment, a bright field image is taken of the region B by the camera 4 using diffused light illumination from the illumination apparatus 5.

In the first to fourth embodiments explained above, illumination by the illumination apparatus 5 is switched over between illumination by diffused light and high-directivity illuminating light by the control unit 7. Whether or not epi-illumination is carried out by the camera 4 is also switched over by the control unit 7. By switching over the illumination methods in this manner, it is possible to easily detect a defect which is irregular such as contamination by taking dark field images, and it becomes possible to measure defect conditions and hue by taking bright field images. In this way, according to edge inspection apparatus of the aforementioned embodiments, it is possible to carry out inspections using the most appropriate illumination by carrying out inspections while switching over illumination methods so as to make the defects it is wished to inspect easy to detect.

Fifth Embodiment

Figure 9:
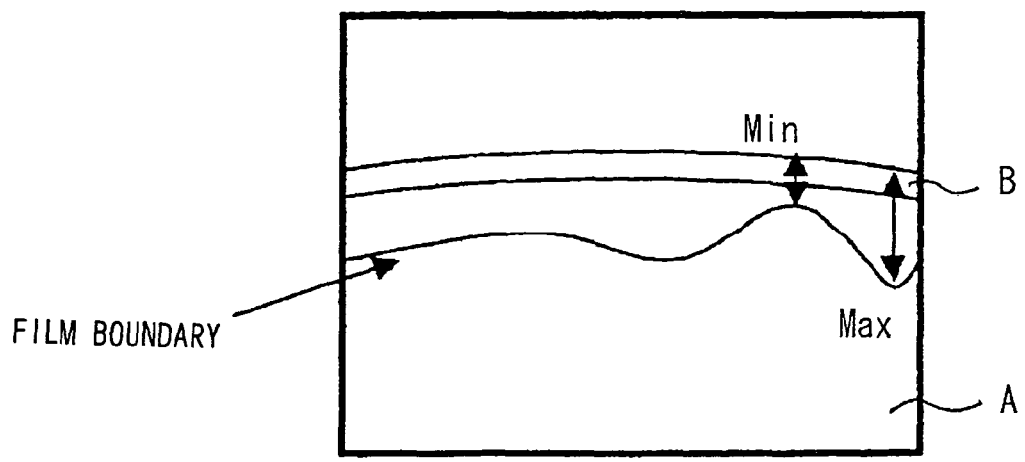
FIG. 9 is a view illustrating a further example of defect inspection using the edge inspection apparatus of the embodiments.

FIG. 9 is a view illustrating a further example of defect inspection using an edge inspection apparatus of the embodiments. A boundary portion of a resist film applied to the surface exists at the surface edge of the semiconductor wafer 1. This boundary region exists at a portion of the region A. FIG. 9 shows an image taken of the boundary portion. Defect detection using images can then be carried out by making comparisons with an image for a non-defective wafer as explained in FIG. 3. In this case, it is possible to determine whether or not a boundary portion of a film is normal by carrying out the processing explained in the following.

At the image shown in FIG. 9, a distance in a radial direction from the boundary portion of the film to an outermost periphery of the wafer edge is obtained at each position on the boundary of the film. The radial direction is in reality substantially the same as the vertical direction of FIG. 9 and it is therefore also sufficient to obtain a distance in the vertical direction. A maximum value for the distance (distance shown by the arrow Max in FIG. 9) and a minimum value (distance shown by the arrow Min in FIG. 9) are then obtained. A maximum value and minimum value are then similarly obtained for a non-defective wafer and a permissible range is decided. These values are then compared and determined whether or not values for the images taken fall within the permissible range so as to determine the quality passing or failing.

It is preferable to carry out this determination of pass or fail using an image by using a color image. In addition to images using the components of R (red), G (green), and B (blue) from a color image, it is also possible to determine pass/fail by obtaining components for H (hue), S (saturation), and I (intensity) from RGB values and using these values to determine pass/fail.

In the first embodiment explained above, as explained in FIG. 5, correction of eccentricity in a state where the semiconductor wafer 1 is mounted on the support table 2 is carried out by moving the semiconductor wafer 1 as a result of being driven by the horizontal drive unit 6. It is sufficient for this correction to correct the relative positional relationship of the camera 4 and the edge of the semiconductor wafer 1. It is therefore possible to carry out correction by moving the camera 4 in a horizontal direction.

It is also possible to correct eccentricity by processing images taken by the camera 4 without changing the physical relative positional relationship of the camera 4 and the edge of the semiconductor wafer 1 (i.e. without moving the semiconductor wafer 1 or the camera 4 in a horizontal direction). The region for the dashed line portion shown in FIG. 5 is made to come to the solid line portion as a result of image processing. In this event, correction of vertical position shift is achieved using image processing but image information for either a top portion or bottom portion in the vertical direction will be lost in the corrected image.

The light source used by the illumination apparatus 5 can be a light source having spectral characteristics in the visible region but a light source having spectral characteristics in the infra-red region can also be used. Further, it is also possible to use a light source having spectral characteristics in the ultra-violet region.

In this embodiment, the camera 4 is installed above the semiconductor wafer 1 and the edge of the surface of the semiconductor wafer 1 is inspected. However, it is also possible to install the camera 4 below the semiconductor wafer 1 so that the apparatus inspects the edge of the reverse surface of the semiconductor wafer 1. It is also possible to install cameras both above and below the semiconductor wafer 1 so that the apparatus inspects the edge of both the upper surface and the reverse surface.

In the above, a description is given of embodiments of the present invention but the present invention is by no means limited to these embodiments. Other modes that can be considered within the scope of the technological concept of the present invention are also incorporated within the scope of the present invention. The target of inspection is not limited to being a semiconductor wafer providing that the target of inspection is a flat subject. The present invention can therefore also be applied to edge inspection apparatus for other subjects such as liquid crystal panels etc.

According to the embodiments of the present invention, it is possible to inspect conditions of an edge of a flat subject in a precise manner.

What is claimed is:

1. An edge inspection apparatus comprising:
a first illumination unit that illuminates an inclined portion of an edge of a flat subject with one of diffused light and illuminating light of a high directivity from a position other than directly above or directly below a surface or a reverse surface of the subject, with the inclined portion being inclined with respect to the surface or the reverse surface of the subject;
a second illumination unit that epi-illuminates a parallel portion of the edge from a position in a direction perpendicular to a plane parallel with the surface or the reverse surface of the subject, with the parallel portion being parallel to the surface or the reverse surface of the subject;
an imaging unit that takes an image of the edge from a position in a direction perpendicular to a plane parallel to the surface or the reverse surface of the subject at the same time; and
an inspection unit that inspects conditions of the inclined portion of the edge, using the image obtained by the imaging unit.

2. An edge inspection apparatus according to claim 1, further comprising:
a control unit that switches illumination light from the first illumination unit between the diffused light and the illuminating light with a high degree of directivity.

3. An edge inspection apparatus according to claim 1, wherein:
the imaging unit takes images of the inclined portion and the parallel portion of the edge at the same time.

4. An edge inspection apparatus according to claim 1, further comprising:
an adjusting unit that adjusts brightness of an image of the inclined portion illuminated by the first illumination unit and an image of the parallel portion illuminated by the second illumination unit taken by the imaging unit so as to be within a range of sensitivity of the imaging unit.

5. An edge inspection apparatus according to claim 4, wherein:
the adjusting unit adjusts conditions for respective images taken by the imaging unit by adjusting illumination light from the first illumination unit and the second illumination unit.

6. An edge inspection apparatus according to claim 1, wherein:
each of a light source for the first illumination unit and a light source for the second illumination unit is a light source having spectral characteristics in an infrared region.

7. An edge inspection apparatus according to claim 1, wherein:
each of a light source for the first illumination unit and a light source for the second illumination unit is a light source having spectral characteristics in an ultraviolet region.

8. An edge inspection apparatus according to claim 1, further comprising:
a rotation unit that rotates the flat subject, wherein:
the imaging unit takes images of the edge of the subject at a plurality of locations.

9. An edge inspection apparatus comprising:
a first illumination unit that illuminates an inclined portion of an edge of a flat subject with one of diffused light and illuminating light of a high directivity from a position other than directly above or directly below a surface or a reverse surface of the subject, with the inclined portion being inclined with respect to the surface or the reverse surface of the subject;
a second illumination unit that epi-illuminates a parallel portion of the edge from a position in a direction perpendicular to a plane parallel with the surface or the reverse surface of the subject, with the parallel portion being parallel to the surface or the reverse surface of the subject;
an imaging unit that takes an image of the edge from a position in a direction perpendicular to a plane parallel to the surface or the reverse surface of the subject; and
an inspection unit that inspects conditions of the inclined portion and the parallel portion of the edge, by comparing an image obtained by the imaging unit and a reference image stored in advance.

10. An edge inspection apparatus according to claim 9, wherein:
the reference image is an image taken by the imaging unit of an edge of a non-defective subject.

11. An edge inspection apparatus according to claim 9, further comprising:
a rotation unit that rotates the flat subject, wherein:
the imaging unit takes images of the edge of the subject at a plurality of locations.

12. An edge inspection apparatus according to claim 11, further comprising:
a movement unit that moves at least one of the imaging unit and the subject in a direction parallel with the surface of the subject; and
a control unit that controls movement due to the movement unit according to a rotation angle position of the subject by the rotation unit.

13. An edge inspection apparatus according to claim 12, wherein:
the subject is circular, and the rotation unit rotates the subject by rotatably driving a mounting unit on which the subject is mounted and detects an amount of shift between a center of the subject and a center of rotation of the mounting unit, and
the control unit controls movement due to the movement unit according to the amount of shift.

14. An edge inspection apparatus according to claim 11, wherein:
the inspection unit specifies a position of defect detected as a result of inspection using a coordinate value within an image obtained by the imaging unit and an angle of rotation due to the rotation unit.

15. An edge inspection apparatus according to claim 10, further comprising:
a rotation unit that rotates the flat subject, wherein:
the imaging unit takes images of the edge at a plurality of rotation angle positions of the subject rotated by the rotating unit, and
the inspection unit compares an image obtained by the imaging unit and the reference image, which was stored in advance, of the edge of the non-defective subject corresponding to a rotation angle position of the image obtained by the imaging unit.

* * * * *